US010185834B2

(12) United States Patent
Adam et al.

(10) Patent No.: US 10,185,834 B2
(45) Date of Patent: Jan. 22, 2019

(54) DEVICE AND METHOD FOR GENERATING AND DISPLAYING GRAPHIC CODES SPECIFIC FOR MEDICAL DEVICES AND MEDICAL TREATMENT

(71) Applicant: Fresenius Medical Care Deutschland GmbH, Bad Homburg (DE)

(72) Inventors: Pascal Adam, Rehlingen-Siersburg (DE); Holger Bluemler, Friedrichsdorf (DE); Danilo Collini, Milan (IT); Juergen Klewinghaus, Oberursel (DE); Bastian Lotz, Giessen (DE); Ingmar Paetzold, Aschaffenburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 14/177,644

(22) Filed: Feb. 11, 2014

(65) Prior Publication Data
US 2014/0230071 A1    Aug. 14, 2014

Related U.S. Application Data

(60) Provisional application No. 61/763,303, filed on Feb. 11, 2013.

(30) Foreign Application Priority Data

Feb. 11, 2013  (DE) .......................... 10 2013 002 231

(51) Int. Cl.
G06F 21/60    (2013.01)
A61M 1/16    (2006.01)
(Continued)

(52) U.S. Cl.
CPC ............... *G06F 21/60* (2013.01); *A61M 1/16* (2013.01); *G16H 10/60* (2018.01); *G16H 40/63* (2018.01);
(Continued)

(58) Field of Classification Search
CPC ................................. G06Q 50/24; G06K 7/14
See application file for complete search history.

(56) References Cited

U.S. PATENT DOCUMENTS 6,676,621 B1    1/2004 Menninger
2002/0198742 A1*  12/2002 Kameda ................ G06F 19/327
                                                                                    705/3

(Continued)

FOREIGN PATENT DOCUMENTS

DE        198 49 787       2/2000
DE    10 2011 011767       8/2012
(Continued)

OTHER PUBLICATIONS

"QR Code" http://en.wikipedia.org/wiki/QR_Code.

*Primary Examiner* — Mahfuzur Rahman
*Assistant Examiner* — Arya Golriz
(74) *Attorney, Agent, or Firm* — Jacobson Holman, PLLC

(57) ABSTRACT

The present invention relates to the field of information display and information playback on medical fluid management machines, in particular dialysis machines in which there should be a simple and reliable transmission of patient features and machine features to a mobile computer. The present invention is based on the problem of making available to the operating personnel information pertaining to the medical fluid management machine or a treatment to be performed therewith and doing so in a simple and convenient manner such that certain information should be readable only by certain groups of people. In this regard methods (Continued)

and devices have been proposed with which specific graphic codes are generated, encrypted and displayed or applied, these graphic codes being inputable and decodable by a mobile computer.

15 Claims, 9 Drawing Sheets

(51) Int. Cl.
  *G16H 40/63* (2018.01)
  *G16H 10/60* (2018.01)
(52) U.S. Cl.
  CPC ... *A61M 2205/50* (2013.01); *A61M 2205/502* (2013.01)

(56) References Cited

U.S. PATENT DOCUMENTS

| | | | |
|---|---|---|---|
| 2006/0206356 A1* | 9/2006 | Vanderveen | 705/2 |
| 2008/0011836 A1* | 1/2008 | Adema | G06Q 10/00 235/383 |
| 2008/0149701 A1 | 6/2008 | Lane | |
| 2009/0031139 A1* | 1/2009 | Geoffrey | 713/186 |
| 2009/0326443 A1* | 12/2009 | Bangera | A61M 5/1723 604/65 |
| 2010/0169120 A1* | 7/2010 | Herbst | G06Q 50/24 705/3 |
| 2012/0067943 A1 | 3/2012 | Saunders et al. | |
| 2012/0185267 A1 | 7/2012 | Kamen et al. | |
| 2012/0191617 A1* | 7/2012 | McIntosh | B29D 30/54 705/308 |
| 2012/0212455 A1 | 8/2012 | Kloeffel | |
| 2013/0026241 A1* | 1/2013 | Sakahashi | G06K 19/06037 235/494 |
| 2013/0177455 A1* | 7/2013 | Kamen | G06F 19/3418 417/313 |
| 2014/0142979 A1* | 5/2014 | Mitsunaga | G06F 19/322 705/3 |

FOREIGN PATENT DOCUMENTS

| | | |
|---|---|---|
| GB | 2 459 686 | 11/2009 |
| WO | WO 03/026558 | 4/2003 |
| WO | WO 2012/078298 | 6/2012 |

* cited by examiner

DEVICE AND METHOD FOR GENERATING AND DISPLAYING GRAPHIC CODES SPECIFIC FOR MEDICAL DEVICES AND MEDICAL TREATMENT

TECHNICAL FIELD

The invention relates to the field of generating and displaying graphic codes, which are based on a medical fluid management machine and/or on a treatment performed using said medical fluid management machine.

BACKGROUND

Medical fluid management machines are understood here in particular to be devices for conducting, treating and/or distributing fluids and/or gases in which a fluid is transported between a patient and a fluid treatment component and/or a fluid source through a fluid line.

Fluid management machines are understood in particular to also include fluid treatment devices such as blood treatment devices in which a fluid from a patient is sent through a fluid line to a fluid treatment component, is treated by the fluid treatment component and is returned to the patient through the fluid line which may be divided into an arterial branch and a venous branch. Examples of such blood treatment devices include in particular hemodialysis machines. One such blood treatment device is the subject matter of DE 198 49 787 C1 by the present applicant, the contents of which are herewith fully included in the disclosure content of the present patent application.

Dialysis is a method for purifying the blood of patients who have acute or chronic renal insufficiency. A fundamental distinction is made here between methods having an extracorporeal blood circulation such as hemodialysis, hemofiltration or hemodiafiltration and peritoneal dialysis which does not have an extracorporeal blood circulation.

In hemodialysis, the blood is sent in an extracorporeal circulation through the blood chamber of a dialyzer, which is separated from a dialysis fluid chamber by a semipermeable membrane. A dialysis fluid containing the blood electrolytes in a certain concentration flows through the dialysis fluid chamber. The substance concentration of the blood electrolytes in the dialysis fluid corresponds to the concentration in the blood of a healthy person. During the treatment the patient's blood and the dialysis fluid are usually passed by both sides of the semipermeable membrane in countercurrent at a predetermined flow rate. The substances that are eliminated in urine diffuse through the membrane from the blood chamber into the chamber for the dialysis fluid, while electrolytes present in the blood and in the dialysis fluid at the same time diffuse from the chamber of the higher concentration to the chamber of the lower concentration. If a pressure gradient is built up on the dialysis membrane from the blood side to the dialysate side, for example, by means of a pump which withdraws dialysate from the dialysate circulation downstream from the dialysis filter on the dialysate side, water leaves the patient's blood and enters the dialysate circulation by passing through the dialysis membrane. This process of ultrafiltration leads to the desired withdrawal of water from the patient's blood.

In hemofiltration, ultrafiltrate is withdrawn from the patient's blood by applying a transmembrane pressure in the dialyzer without passing the dialysis fluid by the side of the membrane of the dialyzer which is opposite the patient's blood. In addition, a sterile and pyrogen-free substitute solution may be added to the patient's blood. We then speak of predilution or postdilution depending on whether this substitute solution is added upstream from the dialyzer or downstream. The mass exchange takes place by convection in hemofiltration.

Hemodiafiltration combines the methods of dialysis and hemofiltration. There is a diffusive mass exchange between the patient's blood and the dialysis fluid through the semipermeable membrane of a dialyzer, while the plasma water is also filtered out by a pressure gradient on the membrane of the dialyzer.

The methods of hemodialysis, hemofiltration and hemodiafiltration are usually performed using automatic hemodialysis machines such as those distributed by the applicant under the designation 5008.

Plasmapheresis is a blood treatment method in which the patient's blood is separated into blood plasma and its corpuscular constituents (cells). The separated blood plasma is purified or replaced by a substitution solution and the purified blood plasma or the substitution solution is returned to the patient.

In peritoneal dialysis, the abdominal cavity of a patient is filled with a dialysis fluid through a catheter guided through the abdominal wall, said dialysis fluid having a concentration gradient with respect to the endogenous fluids. Through the peritoneum, which functions as the membrane, the toxins present in the patient's body cross over into the abdominal cavity. After a few hours the dialysis fluid in the patient's abdominal cavity is spent and is replaced. Water can enter the dialysis fluid from the patient's blood through the peritoneum by means of osmotic processes, thereby withdrawing water from the patient.

The peritoneal dialysis method is usually performed with the help of automatic peritoneal dialysis machines such as those distributed by the applicant under the brand name sleep.safe.

Dialysis machines as an example of complex medical fluid management machines have extensive functions. To control these functions, medical fluid management machines such as dialysis machines are equipped with at least one control unit. These control units may be embodied as a CPU (central processing unit) or as a microcontroller which is programmed by software programs. Such machines are frequently operated by touchscreen displays. Such a touchscreen display combines an input device and an output device in a single surface, thereby providing a touch-sensitive surface with which operator input can be detected.

Possible alternative embodiments include the spatial separation of the input device and the output device, for example, by a conventional display, for example, as a CRT monitor (cathode ray tube), LCD (liquid crystal display), plasma or OLED display (organic light-emitting diode) as the output device and a touchpad, which is spatially separate therefrom and provides a touch-sensitive surface with which operator input can be detected, as the input device.

Embodiments of a medical fluid management machine are to be described below on the basis of a dialysis machine. Examples of this include infusion devices for medical fluids, cardiovascular support machines with an extracorporeal blood circulation, liver support machines with an extracorporeal blood circulation or the like. Each embodiment which is described below on the example of a dialysis machine as an example of a medical fluid management machine can be transferred readily to another medical fluid management machine. Such embodiments are explicitly covered by the accompanying claims.

Patients suffering from renal failure must regularly undergo dialysis treatments. These treatments are performed in the case of hemodialysis or in general in methods in which the blood is purified in an extracorporeal blood circulation, usually under the supervision of medical personnel in a dialysis unit.

Such dialysis units include several dialysis machines within one room and/or a building so that a plurality of patients can be treated at the same time on these machines.

It is important for the attending medical personnel that the identity of each patient being treated is known and is clearly assigned to a certain dialysis machine. Only in this way is it possible to ensure that the specific patient will receive the treatment intended for him.

For this purpose, there are known patient cards for the individual patient. Such patient cards have at least one interface for communication with a corresponding interface on the dialysis machine and have at least one memory unit in which the individual patient's data can be stored.

The individual patient's data may include the name of the patient. In addition, physiological data such as height, age, gender, normal blood pressure, etc. may also be stored there along with data from past treatments such as the date or duration of the treatment as well as settings on the respective machine such as, for example, the blood flow rate, the dialysate flow rate, the solutions and filters used, etc.

At the start of the treatment, the patient announces himself, for example, by entering the patient card into the dialysis machine. During the treatment, the patient's name may be displayed on the screen on the machine.

The personnel can thus see the identity of the patient at one glance. It has proven to be a disadvantage that knowledge of the patient's name alone does not usually allow an assessment of the patient's medical situation. This requires a knowledge of all the physiological and treatment-related data associated with the patient.

This information is usually not displayed on the screen of the dialysis machine. In addition, there are also known medical fluid management machines which do not display the patient's name.

In addition, other information pertaining to the dialysis machine itself or a treatment performed with it or even the overall situation within a dialysis unit is also important in the past had to be made known in a variety of ways to the persons intended to receive the information.

Such specific data may include, for example: the model, the year built and the service life of the machine, advertising information about the machine, information about the maintenance status of the machine, information about the equipment on the machine and/or about the accessory parts on the machine and optionally also error messages. In addition, it may also be important to obtain information about the occupancy of a dialysis unit, i.e., which people are currently being treated on which dialysis machines, what their current treatment status is, for example, how long the dialysis treatment for each patient currently being treated will last or which patients are intended for a treatment within a certain interval of time in the future.

The information that is to be transmitted will be directed at different people, depending on the informational content. Different people may thus have different types of authorization to receive information output by the dialysis machine or not. For example, information pertaining to the maintenance status or error messages on the machine will be directed at technical personnel, whereas medical data will be sent to medical personnel and should be read only by the latter.

In addition, general information, for example, advertising messages may be directed to a third group, for example, to visitors at a professional exhibition.

The operator of a dialysis machine, in particular the attending physician, may carry with him a device which displays the information intended for that physician, and the data for the corresponding patient may be sent to his device or it may have available an apparatus for input of the patient card in order to get an overview of the patient's medical situation.

Such devices may be devices that are specifically designed for this purpose and are usually portable or there may be conventional mobile computers such as smartphones or tablet PCs, which receive the corresponding data over a data interface. In one embodiment, this data interface is based on wireless communication such as Bluetooth, WLAN or mobile radio technology.

DESCRIPTION

The object of the present invention is therefore to create a possibility of establishing the assignment of a patient to a medical fluid management machine and also permitting improved transmission of physiological and/or treatment-related data and/or machine-specific data.

These objects are achieved according to the invention by a method for display of at least one graphic code comprising the steps of encrypting information which is based on a medical fluid management machine and/or a treatment performed or to be performed therewith, using a key which specific for a given person or for a group of people, generating a graphic code based at least in part on the encrypted information, and display of the graphic code.

The objects are further achieved by a method for extracting information based on a medical fluid management machine and/or a treatment performed or to be performed therewith, comprising the steps of entering a graphic code which graphically encode encrypted information which is based on the medical fluid management machine and/or a treatment already performed or to be performed therewith by using a key which is specific for a given person or is specific for a group of people. The information is based on the medical fluid management machine and/or a treatment performed or to be performed therewith. The method further includes decoding the graphic code to recover the encrypted information, decryption of the decoded information to recover the information based on the medical fluid management machine and/or the treatment already performed or to be performed therewith, using the key of the least one graphic code. The code, being specific for a given person or for a group of people, can be recovered, and the information thereby retrieved can be processed further, in particular by display of the decrypted information.

Further, the objects of the present invention are achieved by a method for establishing a correlation between a patient's identity and a treatment station, comprising the steps of generating at least one graphic code which encodes an identification feature of the treatment station and/or of a part that cooperates with the treatment station; applying the at least one graphic code to the treatment station and/or a part thereof, which cooperates with the treatment station; entering the identity of a patient assigned to the treatment station, and transmitting the identity of the patient and the at least one identification feature to an allocation unit.

The objects the present invention are also achieved by a method for determining the identity of a patient who has been treated or is to be treated at a treatment station, comprising the steps of detecting at least one graphic code which is applied to the treatment station and/or to a part that works together with the treatment station and which graphically encodes an identification feature of the treatment station, by a mobile computer; decoding the identification feature which is encoded in the at least one graphic code; transmitting the identification feature to an allocation unit in which the allocation of the patient data to the at least one identification feature was established; and receiving the patient's identity determined on the basis of the allocation to the identification feature.

Still further, the objects of the present invention are achieved by a method for display of graphic codes wherein the graphic codes encode information and wherein different graphic codes are displayed one after the other over a display period and wherein the display period defines the period of time in which the graphic codes are displayed without repetition.

The objects of the present invention are also achieved by a medical fluid management machine having a display device and a control unit wherein the control unit is equipped to encrypt a graphic code containing information based on the medical fluid management machine or a treatment performed or to be performed with it using a key which is specific for a given person or for a group of people and wherein the control unit is additionally equipped to generate a graphic code based on the encrypted information and to display the graphic code on the display device.

The objects of the present invention are further achieved by a system having a medical fluid management machine as just summarized in the previous paragraph and a mobile computer having a control unit, a data interface and a reader for entering graphic codes, wherein the control unit is equipped to decode and decrypt the information encoded and encrypted in a graphic code entered by using the reader.

Still further, the objects of the present invention are achieved by a mobile computer for obtaining information based on a medical fluid management machine and/or a treatment that has been performed or is to be performed therewith by using a control unit, and a reader for reading a graphic code wherein the control unit is equipped to decode information based on a medical fluid management machine and/or a treatment that has been performed or is to be performed therewith, which is encoded and encrypted using the key specific for a given person or a group of people and to decrypt the code using the key that is specific for a given person or a group of people.

The objects are further achieved by a mobile computer for determining the identity of a patient that has been treated or is to be treated on a treatment station, comprising a control unit, a data interface and a reader for reading a graphic code which graphically encodes an identification feature of the treatment station, wherein the control unit is equipped to decode the identification feature encoded in the graphic code, and wherein the data interface is equipped to transmit the identification feature to an allocation unit and to receive a patient's identity from the allocation unit as a result of the transmission.

Still further, the objects of the present invention are achieved by a computer program which can be loaded into the internal memory of at least one control unit and comprises software code sections with which methods steps as described herein are executed when the computer program is running on the at least one control unit, and by a computer program product which is stored on a data medium that is usable in a computer, comprising computer-readable program means with which a computer can execute the methods described herein.

Advantageous embodiments include a plurality of encrypted graphic codes being displayed successively over a display period with the display period defining the period of time in which the graphic codes are displayed without repetition or the display of the at least one graphic code being initiated by an optical signal Further advantageous embodiments include at least a portion of the graphic code being encrypted using a key which is specific for a given person or for a group of people; the identification feature being encoded in the graphic code in encrypted form with the identification feature being decoded and decrypted after being input; the patient's identity being display on the mobile computer; additional patient-related information containing treatment data and/or physiological data being displayed on the mobile computer; the application of the graphic code being performed by applying a stick-on label which is provided with the generated graphic code to the treatment station or to part that cooperate with the treatment station; the graphic code being a flicker code; the information including treatment data and/or the information including the equipment and/or the status of the medical fluid management machine and/or an identification feature that is characteristic of the medical fluid management machine; the medical fluid management machine being a blood treatment machine and being equipped in particular for hemodialysis, for hemofiltration, for hemodiafiltration, for plasmapheresis, or for automatic peritioneal dialysis; and symbols which are variable over a display period being displayed within the graphic code and wherein the display period defines the period of time during which the graphic codes are displayed without repetition.

According to the teaching of the present disclosure, information pertaining to the medical fluid management machine is to be understood as including treatment-related data, in particular recorded measured values such as the blood flow rate, the dialysate flow rate or volumes accumulated during the treatment, such as the ultrafiltration volume or the substitute volume as well as characteristics over one or more treatments of these exemplary values as well as data pertaining to the equipment and/or furnishing and the condition of the medical machine. These include, for example, device identification numbers and/or machine identification numbers, network addresses, MAC addresses, software version numbers, running time of the machine, location of the machine, error messages, installed accessories, connected accessories such as sets of tubing, bags, filters, drip chambers and the like as well as advertising or general information pertaining to the fluid management machine.

Medical fluid management machines such as dialysis machines often have at least one control unit. Such a control unit controls the components of the medical machine on the basis of their parameter values which are made known to the medical machine and characterize it. Such control units are often equipped with programmable microprocessors or microcontrollers, such that the programs controlling them are stored in program data memories provided for this purpose.

A control unit may be implemented on one or more processors. Several control units are thus often kept available in a medical machine. In the sense of the present disclosure, the term "control unit" is also understood to include a plurality of control units.

In addition, medical machines such as dialysis machines often have sending and receiving devices, where sending and receiving devices are understood to include all devices with which data, in particular digital data can be sent to and/or received from a remote device. This includes in particular data interfaces such as network interfaces which may be hardwired (for example, RJ45) or wireless (for example, WLAN, Bluetooth, infrared or UMTS).

In addition, medical machines may also have input devices for entering graphical information such as images or barcodes. Such input devices may include scanners or cameras.

A patient undergoing a dialysis treatment often suffers from chronic renal failure. This means that he must regularly undergo treatments which may last several hours per treatment.

During a dialysis treatment, the patient's blood is purified and excess water is removed from the patient's blood. The success of the treatment depends on a variety of factors and is usually tracked by the dialysis machine. This physiological data such as the arterial blood pressure and the venous blood pressure in the extracorporeal blood circulation or the blood temperature and other values pertaining to the treatment such as the flow rates of blood and dialysis fluid as well as the ultrafiltration rate and/or the substitution rate and accumulated volumes of these fluids can be recorded over time and stored as a data record.

During the treatment, the identity of the patient may be made known to the dialysis machine. This may take place, for example, in that the patient has an individual patient card which can be entered into the dialysis machine using a corresponding reader device.

Such patient cards are so-called Smart-Cards, which have a memory device and an interface. Patient data such as the name of the patient, physiological data such as height, age, gender and so-called dry weight may be stored in the memory unit.

The dry weight is the body weight of a patient which the patient should usually have after a dialysis treatment. Because of their renal failures, patients who depend on dialysis often do not eliminate enough water or any at all. Due to the need to ingest water with food, the patient thus accumulates water in his blood and in his body tissues, which should be removed by the ultrafiltration process during dialysis. As a rule, the volume that should be removed is determined from the difference between the patient's current body weight and his saved dry weight.

In addition, data from past treatments may also be stored on the patient card, for example, the date of the last treatment, the duration, the devices used, which determine the treatment, such as filters, solutions, therapeutic data such as the ultrafiltration volume, blood flow rates and accompanying physiological measured values such as the blood pressure, body temperature, etc. These data can then be updated by writing one's own internal memory.

The interface of the patient card may be designed in a variety of ways, for example, as magnetic strips or contact surfaces which may enter into an electrically conductive connection with a reading device or reader. Patient cards may also be equipped with noncontact interfaces such as RFID systems. To be readable and/or writable on the greatest possible number of devices, patient cards may also be equipped with a number of different interfaces, which may be used alternatively or even simultaneously.

In addition to a memory, patient cards often also have at least one control unit, which is usually designed as a microprocessor and/or microcontroller and is programmed with software accordingly for interaction with devices provided for this purpose. This programming may be stored in the internal memory. The programming may also be revised and/or updated by saving a new version.

The patient card may also have a plurality of control units.

The patient may also make himself known on the dialysis machine in another way. In this regard, it is possible to access any method which permits an unambiguous identification of the patient.

For example, the patient's name may also be entered manually via an operator input on the dialysis machine, for example, by a virtual keyboard which is displayed on a touchscreen.

To avoid mix-ups, such an input of the patient's name may be confirmed by additional input of a password by the patient himself.

Another possibility is the input of biometric data about the patient to unambiguously identify the patient. Such biometric data may include, for example, facial recognition of the patient or his fingerprint. Corresponding devices, for example, cameras or fingerprint scanners, may be provided in the dialysis machine for detection of such features.

To unambiguously identify the patient after input of such biometric data, it is necessary for the link between the detected biometric data and the patient's identity to be stored. This storage may be in the dialysis machine itself, for example, through a data record stored in an internal memory of the dialysis machine or advantageously in a remote device, for example, a server computer, which can communicate with the dialysis machine via a remote data transmission.

Another possibility of identifying the patient unambiguously is for a graphic code to be kept for the patient, this code being generated on a patient-individual basis. Such a patient-individual graphic code may be, for example, a barcode or a QR code (quick response code), which is more complex than a conventional barcode, and consequently it offers more extensive coding options. The QR code is a two-dimensional code. Other two-dimensional codes include the micro QR code, the secure QR code (SQRC) and the iQR code. However, any graphic codes that can be assigned individually to a patient are consistent with the teaching of the present invention.

To identify the patient, in one embodiment, the graphic code kept for the patient is entered into the dialysis machine. The graphic code may also be present on a patient card, for example. The dialysis machine may use a camera, for example, which is provided for this purpose for entering the graphic code, or it may use a barcode scanner.

The graphic code may contain the patient's name graphically encoded or any other identification feature, for example, a patient number which is linked to the patient's identity. However, the graphic code may also be individual for the identity of the patient. In this case, the graphic code input is compared with the saved codes, such that the saved codes are each linked to individual patient data. In this way, the graphic code input can be assigned unambiguously to the data of a certain patient.

Regardless of how the identity of the patient is made known to the dialysis machine, it is provided in accordance with the teaching of the present invention that an unambiguous allocation of the patient's identity to the respective dialysis machine is made.

To generate an unambiguous allocation between the patient and dialysis machine, it is also provided that the dialysis machine here also has unambiguous identification features. Individual machine numbers or fixed IP addresses under which dialysis machines in a data network communicate or MAC addresses (media access control addresses)

which unambiguously identify the hardware of dialysis machines are suitable for this purpose.

Such identification features are usually kept in the dialysis machine and can be transmitted by remote data transmission to a remote device, for example, to a server computer.

Thus if a patient is identified to the dialysis machine in one of the ways described above, then the patient's identity and/or a data record linked to the patient's identity as well as the identity of the dialysis machine may be sent to a remote device, for example, to a server computer. The two identities are linked together in the dialysis machine and also in the server computer. There is a pairing of these individual data in this way.

Pairing of the patient's identity with the identity of the dialysis machine may also occur, in that the patient's identity and the identification features of the dialysis machine are entered into a mobile computer, and these data are sent from the mobile computer to a remote computer, for example, a server computer, where they are linked together. This is advantageous if the dialysis machine does not have a data link to the remote computer or does not offer a possibility for entering patient identities because it does not have a data interface and/or there is no possibility for input for the patient's identity and/or it does not have a reader for a patient card.

The patient's identity may be entered into the mobile computer input by reading an individual patient's graphic code, which the patient carries on his person. However, the mobile computer may also be equipped with means for reading a patient card for this purpose.

In addition to the individual patient data, data linked to the identity of the dialysis machine may also be saved in the server computer.

Such data may include the following: the location of the dialysis machine, the owner of the dialysis machine, information about equipment on the dialysis machine, the maintenance status of the machine, messages about malfunctions that can be sent from the dialysis machine to the server computer, the operating time of the machine, etc.

There are usually several dialysis machines in one dialysis unit, so that a plurality of patients can be treated at the same time on these machines. In agreement with the teaching of the present invention, all patients may be identified to the respective dialysis machines by one of the methods described above, and all dialysis machines may send the patient identification features as well as the dialysis machine identification features to a remote server computer.

By saving these data in a server computer, information about the current occupancy of the dialysis unit, optionally with all the relevant, therapeutic and machine-specific data may be kept on hand in this computer. This information may be sent to other devices in accordance with the teaching of the present invention.

Such a device may be kept on available by the attending medical personnel or by the technical personnel.

Such a device may be, for example, a mobile terminal such as a smartphone or a table PC and is referred to below as an external computer.

Such external computers usually have not only interfaces for data communication but also cameras, which can be used to enter so-called graphic codes. The graphic codes entered may be decoded in the external computer. To do so, the external computer uses a special computer program. Such computer programs are referred to as applications or just "apps" for short, in particular with smartphones or tablet PCs.

The patient can also have such a graphic code available in the manner described above. Furthermore, the dialysis machine may have such a code, for example, as a stick-on label.

The embodiment as a stick-on label has the advantage that it is simple to manufacture and apply. Such a stick-on label may be attached to the dialysis machine at any location, but advantageously in such a way that it is easily to read.

The information contained in the graphic code may be displayed in an encrypted form. This may be done, for example, by using a secure graphic code, for example, the secure QR code. The secure QR code (SQRC) is a QR code in which the data content or parts thereof should not be entered by a third party. Some or all of the coded data is encrypted with the SQRC for this purpose. The public (unencrypted) data in an SQRC may also be read using normal reader devices, such as mobile computers, whereas the encrypted information remains hidden with these normal readers. To be able to read this information, the reader must have special software which is available via an individual key, for example, a password which is also used in generating the encrypted information. This key may be issued individually by the information provider to different groups of people.

Within a graphic code, information directed at a number of groups of people may be encrypted by using multiple keys. Then each group of people will have their own key and may thus decrypt only that part of the encrypted information that is provided for them. Individual people may also have multiple keys.

In accordance with the teaching of the present invention, the nonvolatile labeling may also be produced for parts belonging to the treatment station and applied to the respective part or provided with it.

A treatment station is defined in one embodiment by the dialysis machine with all the accessory parts necessary for the pending treatment such as filters, sets of tubing, medical solution containers, etc. as well as a patient bedding device such as a chair, a couch or a hospital bed and with all the accessory equipment kept on hand for the respective dialysis treatment, for example, EKG equipment, blood pressure monitors or the like.

The respective graphic code is typically individual and characteristic of the respective part provided with it. In addition, it is possible to store information about when parts carrying a graphic code are cooperating. This may take place in the sense of the present invention in that all the parts of a treatment station are identified by an external computer by input of the graphic code and the data records thereby obtained are linked together. The information about the linked parts of a treatment station may be sent to a server computer, for example, by remote data transmission to a remote device, for example.

In this way, the information about which parts of a treatment station work together is generated at one central location, namely the server computer. This information may also be sent to a mobile computer when this has first identified at least one part of the treatment station by entering the applied graphic code, and the identification feature has been sent to the server computer as described above because all the parts of the treatment station are linked together in the server computer through data technology.

A typical procedure for unambiguous identification of the patient during a dialysis treatment provides that the patient is identified on the dialysis machine, for example, by entering his patient card. The dialysis machine then sends the identification features of the patient and of the dialysis machine to a server computer by remote data transmission. The identity of the patient and that of the dialysis machine are stored together, i.e., linked together in the server computer, which is configured as an allocation unit. In addition, additional data records may also be allocated to this pairing of identities. Such data records may comprise information pertaining to therapeutic and/or medical and/or physiological data on an individual patient or data about the dialysis machine, its equipment or the dialysis unit in which the dialysis machine is located.

The medical staff who carry an external computer, for example, a smartphone or a tablet PC with an integrated camera, can enter a graphic code which is applied to a part of the treatment station by using the camera on the smartphone, etc. Through appropriate programming, the external computer decodes the graphic code and thus obtains an identification feature of this part. This identification feature may then be transmitted to the server computer by remote data transmission. The data exchange between the mobile computer or dialysis machine and the server computer may be wireless. Suitable wireless data transmission methods include wireless transmission such as WLAN and Bluetooth or infrared data transmission.

In all possible exemplary embodiments, data transmission protocols, which are reliable with regard to confidentiality, authenticity and integrity, are preferred for the transmission of data and include, for example, such data transmission protocols as IPSec (internet protocol security) or VPN (virtual private network) or OpenVPN.

In addition, a data transmission protocol with secure identification of interchangeable devices such as Bluetooth or IRDA (infrared data association) may be used for authentication of the dialysis machine and of the mobile computer.

In one preferred embodiment, the graphic code which is applied to the dialysis machine or to the patient bedding device is entered because both devices are always assigned to the same treatment station in the usual forms of treatment.

After the server computer has received the entered identification feature from the mobile computer, the server computer can check the authorization of the mobile computer. This may be accomplished, for example, by checking an identification feature of the mobile computer that is sent along at the same time such as a fixed IP address or a MAC address. To this end, the identification features of several mobile computers are stored in the server computer together with the authorization information associated with them.

It is possible in this way to ascertain whether the mobile computer is authorized for receiving data packets and/or which data packets of the mobile computer it is authorized to receive.

Depending on the authorization, the server computer may send data packets back to the mobile computer. These data may comprise information pertaining to patient individual therapeutic and/or medical and/or physiological data or data pertaining to the dialysis machine, its equipment or the dialysis unit, where the dialysis machine is located. Then the user of the mobile computer can have access to this data.

For example, the patient's name may be displayed on the display of the mobile computer or the occupancy of the dialysis unit or an overview of the past dialysis treatments the patient has received may be displayed in the form of a treatment history.

It is possible in this way, merely by entering a graphic code on the treatment station, to make available extensive information to the medical or technical personnel without requiring direct communication between the dialysis machine and the external mobile computer.

This has advantages in particular with regard to the safety of the dialysis treatment. An exchange of data between the dialysis machine and the external mobile computer would entail the risk of unwanted influence on the dialysis treatment, for example, due to malware, i.e., malicious software, running unbeknownst on the mobile computer.

Such malicious software includes, for example, virus programs or Trojan horse viruses, which can be executed in the mobile computer without being noticed by the user and often have the goal of disrupting computer operations or the programming of the computer or obtaining personal data such as passwords by spying and then transmitting such information to third parties.

Such programs are transmitted by remote data transmission to other devices, where they can cause damage. According to one embodiment in accordance with the teaching of the present invention, such malicious software cannot be transmitted directly from the mobile computer to the dialysis machine because there is no direct data exchange between them. Server computers however which do communicate with the mobile computers and the dialysis machines, are subject to special security precautions by technical personnel specially trained for this purpose.

Such personnel will always be equipped with current programs for defending against malicious software and therefore are especially reliable. It is thus possible to rule out with a high probability that malicious software can spread further via the server computer.

The proposed method for identification of a patient and/or for a simple method of obtaining information about a patient or about a treatment performed on a patient can be transmitted to any treatment station regardless of whether it is associated with a fluid management machine. Thus a treatment station may also be a hospital bed within a hospital to which a graphic code is applied, thereby encoding an unambiguous identification feature of the hospital bed. A physician or some other medical personnel may receive information with regard to the identity of the patient lying in this hospital bed by the method already described above or may receive other information pertaining to the treatment of the patient. In this regard, as already explained, the assignment between the patient and the hospital bed and optionally additional information assigned to the patient and/or to the hospital bed may be stored in a server computer.

After the graphic code has been entered via a mobile computer and decoded, the unambiguous identification feature of the hospital bed can be sent from the mobile computer to the server computer which then subsequently can send the information assigned to the patient and/or to the specific hospital bed back to the mobile computer.

Establishing the correlation between the patient and the hospital bed and/or the treatment station in the server computer which is configured as an allocation unit is done, for example, during central acquisition of patient data on admission of the patient to the hospital.

According to another embodiment, a graphic code is generated dynamically in the dialysis machine and is displayed on the display device which is often designed as a touchscreen display.

The information which is thereby encoded may be any type of information. However, information which is specific for a medical fluid management machine or a treatment performed with said machine is especially preferably encoded.

The information that is generated dynamically may be encoded with encryption in the manner already described above. It is possible in this way to be sure that the information can be read only by the persons authorized to do so.

In general, it may happen that the abundance of information that can be encoded within a single graphic code is not sufficient to encode all the desired information.

Therefore, another object of the present invention is to create a method with which the abundance of graphically coded information can be further increased.

This object is achieved according to the invention by a method having the features of Claim 20. An advantageous embodiment is the subject matter of Claim 21. It is thus provided that different graphic codes can be displayed one after the other over a display period. Several individual different graphic codes may be displayed one after the other in this way. Each individual graphic code may encode different data. The abundance of information to be displayed can be increased in this way. A display period comprises the duration of the display of various graphic codes without repetition, such that the different graphic codes are typically displayed promptly or without any intended pause one after the other. Such a sequence of individual graphic codes corresponds to a film like the display of individual images. The graphic codes displayed there each encode parts of information belonging together.

In another embodiment, the graphic code may contain uncoded graphic symbols. For coding data using a graphic code, it is not always necessary to use all the available display area for coding these data. It is thus possible to use a portion of the display area for other purposes, for example, for display of graphic symbols or plain text. Graphic symbols may include, for example, company logos, images or pictograms.

If several graphic codes are displayed one after the other in the manner already described, then each individual graphic code may be furnished with another uncoded image. A moving film which is visible for the observer can be displayed in this way.

Such a film may include, for example, symbols which symbolize to the user the duration of the film, i.e., the start and stop of the film. Such a symbol may be, for example, an hourglass with a variable sand level.

It is possible to symbolize to the observer in this way how long he must keep the camera and/or the input device of the mobile computer on the graphic codes displayed in order to enter all the coded information. However, the film of symbols displayed can also be used for advertising purposes.

The display of the graphic codes can also be initiated by a signal sent out by the mobile computer. In one embodiment, such a signal is an optical signal, for example, a flashing light, which is often part of a smartphone or tablet PC. The dialysis machine can detect the transmission of this signal with a corresponding sensor (photodetector, camera) and can then cause a graphic code to be displayed.

In another embodiment, the display of graphic codes on the dialysis machine may also be initiated by the display of graphic codes on the mobile computer entered by the dialysis machine. To do so, a graphic code which is displayed on the display device of the mobile computer or is applied as a stick-on label to the mobile computer is saved for a corresponding reading device on the dialysis machine, which may include a camera.

The dialysis machine in this case has a corresponding decoding software and optionally also decryption software, which decodes and/or decrypts the graphic code entered. This has the advantage that the identity of the user of the mobile computer can be encoded in the graphic code input, and the generation and display of graphic codes on the display device may thus be designed on the basis of the individual user.

The user may also be identified to the dialysis machine by any other method already described above. Depending on the identity of the user, the dialysis machine can then generate different graphic codes for each individual person or group of people, and these codes may in turn be additionally encrypted.

Due to the fact that there is no direct network connection between the dialysis machine and the mobile computer in many embodiments, there also cannot be a direct influence on the dialysis machine by the mobile computer. In particular malicious software cannot be transmitted directly. This increases the security of the treatment.

In accordance with the teaching of the present invention, the dynamically generated graphic code can code all information that can be coded with a (static) graphic code embodied as a stick-on label.

The information coded in the graphic code displayed may comprise the following, for example:

Hyperlinks, referring to Internet addresses: Such Internet addresses can address pages where databases are to be found which are specific for the respective machine. However they may also refer to expert forums or expert databases (Expert Wiki) or to pages offering consumer materials or replacement parts or services.

Treatment-related data, such as physiological values or machine settings: The uncoded display of other data on the display device can be reduced through coded display of such data. This yields a much less confusing picture for the patient on the display device. In many cases there are also so-called preliminary alarms in treatment which could upset the patient if displayed as plain text. Coding in the graphic code prevents the patient from being upset in this way.

Furthermore, personal data on the patient can be rendered unreadable for a human observer without assistance. However, the medical personnel will have a suitably programmed mobile computer which provides the means for rendering the coded data legible. This protects the patient's privacy, while at the same time enabling the display of medical data for authorized persons.

In one embodiment, the degree of detail of the coded data may vary according to the authorization of the user. For example, the display for a dialysis physician may be more detailed than that for a dialysis nurse. The type of data encoded in the graphic code may also vary in generating the dynamic graphic code after the user has identified himself to the dialysis machine by any method. When a service technician logs on, preferably technical data are encoded, but when medical personnel logs on, preferably medical data are encoded.

Many treatments are also performed at night or in a period when the patient is asleep. It is advisable here to reduce the brightness of the display device. By displaying a graphic code, which contains all the information displayed in plain text during normal operation, the remaining display area may be switched to be completely dark, so that this will cause only minimal disturbance for the patient. In addition, the contrast of the graphic code may also be reduced.

In another embodiment, the graphic code may also be displayed on another separate display device on the dialysis machine. With the help of a holder designed specifically for this purpose, a mobile computer may be permanently equipped with its reading device aimed at the graphic code. Data can therefore be transmitted from the dialysis machine to the external computer, decoded there and processed further without any feedback effect from the mobile computer on the dialysis machine. Further processing of the data in the mobile computer may include the display of the information of a display device of the mobile computer, which may also include forwarding decoded information to additional devices, for example, to a server computer, a ward computer or a pager for medical personnel. This is advantageous in the case of alarm messages in particular.

The graphic code displayed may also contain information about the required expendable material, pending service activities or necessary repairs. The mobile computer may be programmed so that after successful decoding and optional decryption of the information, it will deliver orders itself or schedule service technicians. This may be performed, for example, by SMS (Small Message Service) or email message to a service technician or by an automated order with a certain provider of consumable materials. The mobile computer may access the Internet in the process and/or may have a mobile radio device. This is advantageous in particular when the treatment is being performed at the patient's home, as is often the case in peritoneal dialysis. In many cases, a hemodialysis treatment is then also performed at the patient's home. The user of the mobile computer in such cases is then often the patient himself although the patient usually lacks the competence to respond correctly to all the messages on the dialysis machine.

In home dialysis, treatment-related data may also be transmitted to a third party, for example, to medical personnel that can respond appropriately if needed. For example, a dialysis physician may contact the patient to take additional measures to speak with him after evaluating the data thereby transmitted.

In another embodiment, the mobile computer may be equipped with a reading device, for example, a camera, to enter and decode the graphic codes applied as stick-on labels to parts of the treatment station. In this way, the information concerning which parts belong to a treatment station can be obtained. This information may be contained in the graphic codes applied to each part. The mobile computer may in turn generate a graphic code which codes for the information about which parts have been entered. This graphic code may in turn be transmitted by the dialysis machine by saving, entering and decoding the graphic code displayed by a reading device, for example, a camera.

For generating optionally encrypted graphic codes and for decoding and optionally decrypting graphic codes, both the dialysis machine and the mobile computer are specifically programmed.

This specific programming includes computer programs which may be loaded directly into an internal memory in the mobile computer and/or in the dialysis machine and may include software code sections which execute the methods described here when the programs are running on the mobile computer or on the dialysis machine. The computer programs may be stored on data media as computer program products, which include computer-readable program means. These data media can be entered into a computer and may also include storage within networks such as the Internet, to which the user can have access, in addition to physical memories such as diskettes, CD ROMs, memory cards, USB sticks or DVDs.

BRIEF DESCRIPTION OF THE FIGURES

Additional details and advantages of the invention will now be described in greater detail on the basis of exemplary embodiments depicted in the drawings, in which.

DETAILED DESCRIPTION OF THE FIGURES

Figure 1:
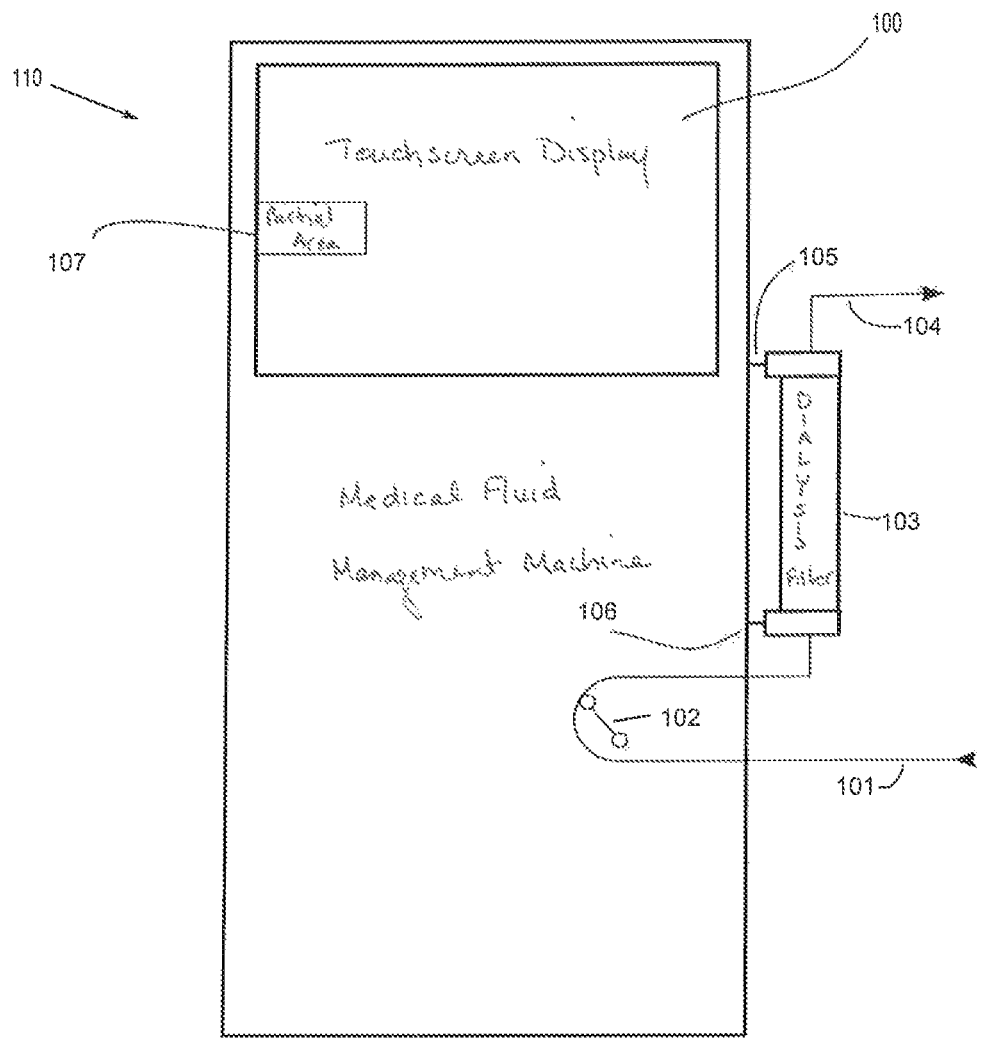
FIG. 1 shows a medical fluid management machine in accordance with the teaching of the present invention, shown as a dialysis machine as an example.

FIG. 1 shows schematically one embodiment of a medical fluid management machine 110 as a hemodialysis machine with a touchscreen display 100. The dialysis machine 110 shows merely by indication parts of an extracorporeal blood circulation with an arterial blood line 101 which drains off the blood of a patient (not shown). The blood pump 102 conveys the blood through a dialysis filter 103, which is equipped with a semipermeable membrane that separates the extracorporeal blood circulation from a dialysis circulation in a semipermeable manner. The treated blood is returned to the patient through the venous line 104. Dialysate is pumped from the dialysate lines 105 and 106 through the dialysis filter 103, where a diffusive mass exchange with the blood of the patient takes place through the semipermeable membrane of the dialysis filter 103. If a pressure gradient is additionally built up from the blood side of the dialysis filter to the dialysate side of the patient, plasma water is expressed out of the blood and into the dialysate. The expressed plasma water is also known as ultrafiltrate. Water can thus be removed from the patient's blood in this way. The dialysate is prepared in the hemodialysis machine 110 and discarded after use. The touchscreen display 100 has a partial area 107 on which graphic codes can be displayed in accordance with the teaching of the present invention.

Figure 2:
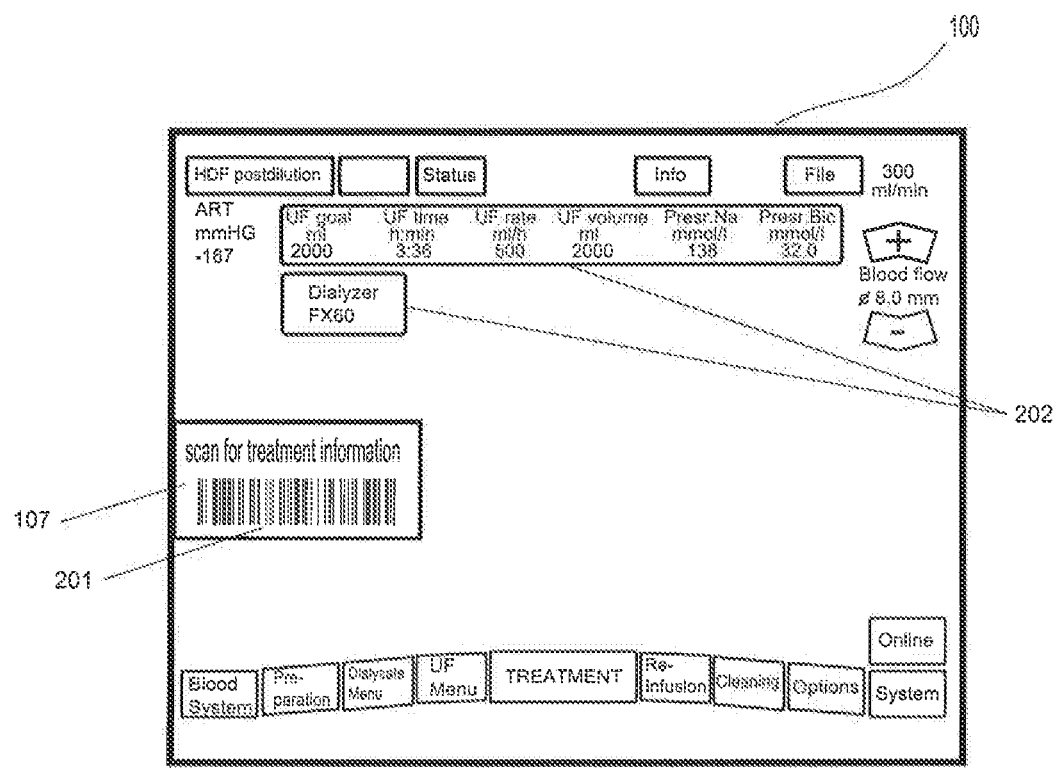
FIG. 2 shows an embodiment of the display screen contents of a medical fluid management machine in accordance with the teaching of the present invention.

In FIG. 2 the touchscreen display 100 is shown in greater detail with an example of screen contents in accordance with the teaching of the present invention.

This example of display screen contents is typical of a hemodialysis machine and illustrates the situation at the end of the treatment. The reference numeral 202 indicates informational displays which typical of a hemodialysis treatment and characterize it. These informational displays provide information about the total quantities of ultrafiltrate withdrawn from the patient, the dialysis filters used or the duration of the treatment.

Figure 3:
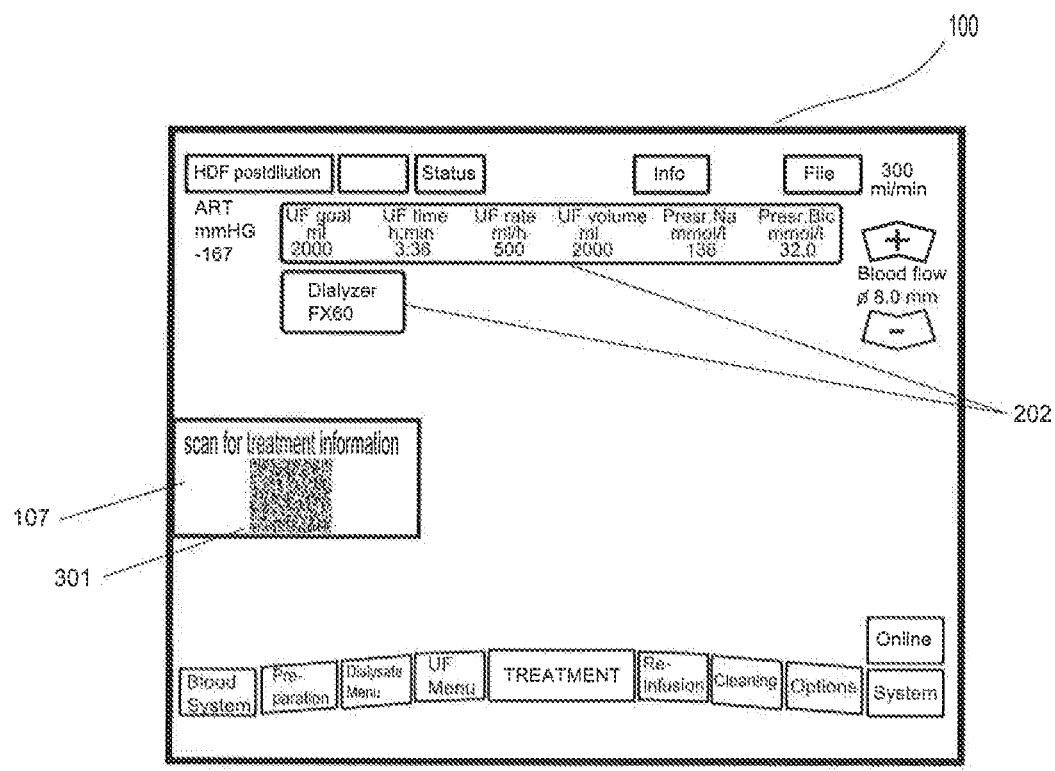
FIG. 3 shows another embodiment of the display screen contents of a medical fluid management machine in accordance with the teaching of the present invention.

In FIGS. 2 and 3, the end of the treatment is indicated by the fact that the values of the displays for the ultrafiltration goal (UF goal) and the current ultrafiltrate quantity (UF volume) are the same.

A graphic code which is shown in FIG. 2 as barcode 201 and in FIG. 3 as QR code 301 is displayed in field 107. In addition, all the graphic codes that can be displayed, for example, including a flicker code are conceivable. The flicker code operates with pulses of light which can encode data; this code has become known, for example, by the ChipTAN method in online banking.

In accordance with the teaching of the present invention, it is provided that the graphic code displayed may encode information that is specific for the medical fluid management machine shown as a dialysis machine in FIG. 1, or a treatment performed using this machine.

Figure 4:
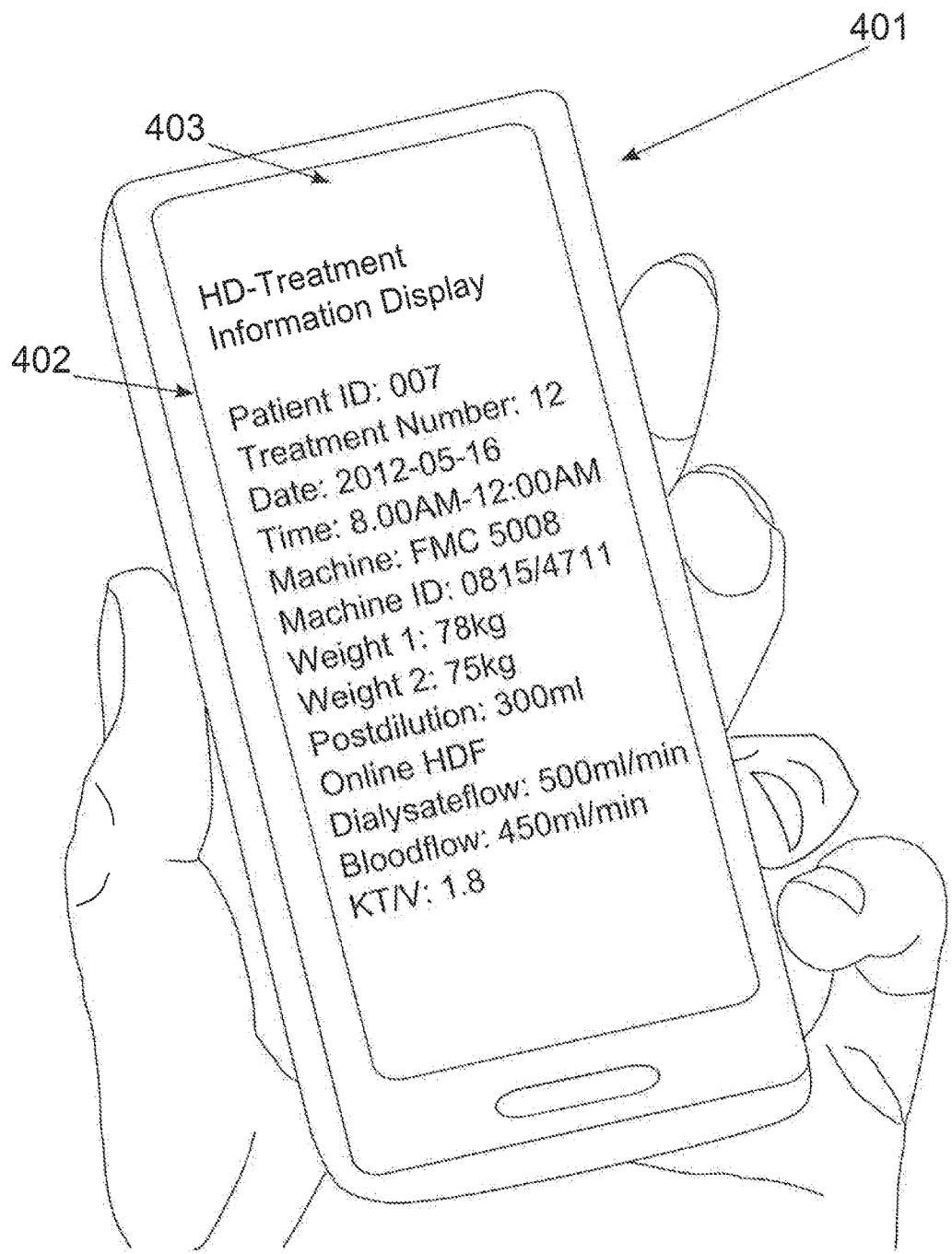
FIG. 4 shows an embodiment of a mobile computer, embodied here as a smartphone, with display screen contents as an example in accordance with the teaching of the present invention.

FIG. 4 shows a mobile computer 401 embodied as a smartphone on whose display device 403 information determined on the basis of graphic codes 201 or 301 is displayed. The operator must first enter the graphic code 201 or 301 using a reader device on the computer 401. Such a reader device is typically a camera (not shown in FIG. 4). Today most smartphones are equipped with at least one camera.

Instead of a smartphone, the portable device may also be a tablet PC or a device constructed specifically for this purpose.

The control unit of the mobile computer 401 decodes the information which is encoded by the graphic codes 201 or 301 input and does so using software installed for this purpose, and it can display this information on the display screen. Thus there is further processing of the information encoded by the graphic code. This further processing of information may also include, in addition to simply displaying the information, the storage of information, sending the information by data transfer, for example, as email or graphic display of the course of the information pertaining to the treatment. The possibilities of further processing of the information are also as varied as permitted by the equipment of the portable device 401 in combination with the stored software.

The information displayed in FIG. 4, for example, pertains to the patient, who is characterized by a patient number (patient ID), as well as the circumstances of the treatment, such as the day's date (date), the time of the treatment (time), the type and running number of the dialysis machine (machine, machine ID). In addition, certain treatment-related information is displayed, such as the weight of the patient at the beginning of the treatment (weight 1) and the weight of the patient at the end of the treatment (weight 2), the type of treatment (HDF, corresponding to hemodiafiltration) with postdilution (postdilution), dialysate flow rate (dialysate flow), blood flow rate (blood flow) and dialysis dose (KT/V). The dialysis dose is of crucial importance for the efficacy of a dialysis treatment and is composed of the product of the clearance K of the dialysis filter and the elapsed time T, this product being weighted (divided) by the urea distribution volume V of the patient. DE 10 2006 032 926 by the present applicant provides additional information in this regard.

It is advantageous in accordance with the teaching of the present invention that this information, which is displayed by the display device 403, need not be encoded directly in the graphic code 201 or 301. It is sufficient that an identification feature, which is characteristic of the medical fluid management machine, is encoded in the graphic code 201 or 301. The mobile computer can decode this characteristic identification feature and transmit it to a remote computer, for example, a server in which the information to be displayed is linked to the characteristic identification feature. In this regard, the remote computer can receive the corresponding information in advance by remote data transmission from the medical fluid management machine itself. The remote computer sends this information to the mobile computer, where it can be displayed. In this way there is little or no direct influence of the mobile computer on the medical fluid management machine because a direct data transmission from the mobile computer to the medical fluid management machine is not necessary. In this example, the data transmission is optical from the medical fluid management machine to the mobile computer through the display of the graphic code and/or from the medical fluid management machine to a remote mobile computer, which may be designed to be especially secure with regard to the integrity of the data link, and from the remote computer to the mobile computer, but not or not necessarily from the mobile computer to the medical fluid management machine.

The information shown in FIG. 4 is given only as an example of a treatment performed with a hemodialysis machine. Any other information that is specific for the respective medical fluid management machine and/or a treatment performed with it may also be displayed.

Figure 5:
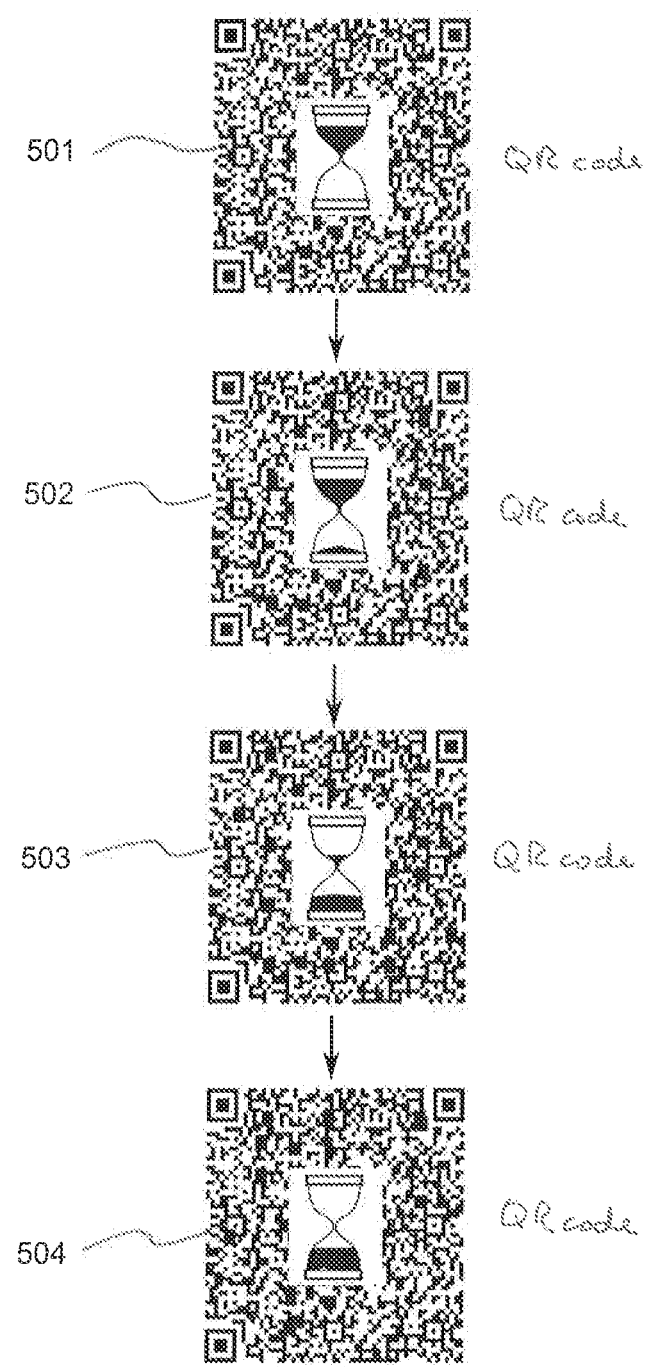
FIG. 5 shows a symbolic representation of a flow chart in the display of several different graphic codes with a variable symbol contained therein in accordance with the teaching of the present invention.

FIG. 5 shows several different QR codes 501 to 504, each with a symbol recognizable by the human eye, shown here as an hourglass with different filling levels.

The QR codes 501 to 504 are displayed one after the other in a sequence and on the whole encode more information than would be possible with just one single QR code. For the user it is helpful to know when the sequence has been completely displayed. This is indicated to the user by the stylized hourglass, which characterizes the beginning and the end of the sequence in the sense of a process. Any symbols or plain text is/are also possible, for example, including company logos for advertising purposes which may even be shown as animation in which a modified logo is displayed for each QR code displayed.

Figure 6:
FIG. 6 shows a symbolic representation of the graphic code displayed and the decoded information from that which pertains to the equipment and the status of a dialysis machine in accordance with the teaching of the present invention.

FIG. 6 shows an example of a graphic code 601, shown here as QR code, and an example of an equipment and status list 602, which is encoded by code 601, as an additional exemplary embodiment of the information that can be encoded by graphic codes.

This equipment and status list 602 comprises the identifiers for a machine key, the machine identification number, the MAC address of the control unit of the medical machine, the software number, the equipment options, additionally installed equipment modules, other equipment and the running time of the medical machine, for example.

In addition, error messages may also be encoded and forwarded in this way.

This information can be decoded by the mobile computer in the manner already described and/or forwarded to a third remote device, for example, a mobile telephone or an email address of a service technician and in the service case this then serves as information for the service technician.

The service technician can then get an idea in advance of the error case and/or the concrete embodiment of a medical machine on the basis of the information forwarded to him and can thus be prepared precisely for the service operation accordingly and can bring along appropriate replacement parts, for example, for the medical machine.

In any case the graphic code displayed may be encrypted. Depending on the authorization of the user entering this graphic code, different information may be released.

Figure 7:
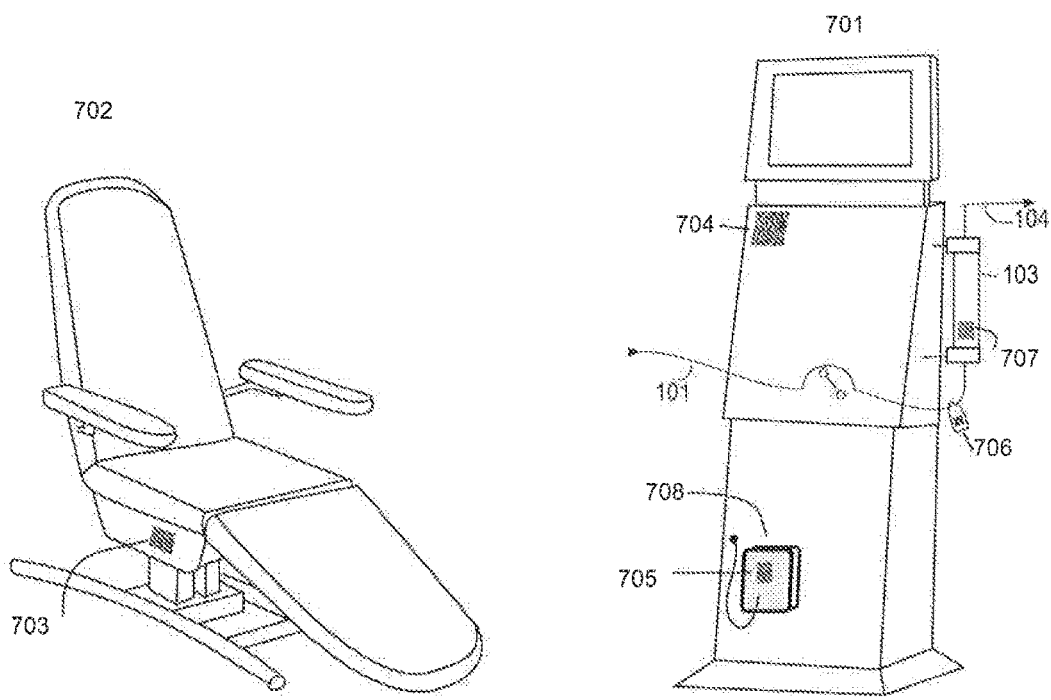
FIG. 7 shows a symbolic representation of a treatment station with stick-on labels applied, having a graphic code, in accordance with the teaching of the present invention.

FIG. 7 shows a typical treatment station consisting of a patient bedding device 702, embodied here as a treatment chair, and a hemodialysis machine 701 like that in FIG. 1. For example, various parts of the treatment station are provided with applied graphic codes 703 through 707.

The graphic codes are generated individually for each part of the treatment station, for example, by printing out QR codes on stick-on labels such that the relevant information such as device numbers or part identification numbers, model, design year and/or other information can be encoded by the QR code which must also then be encrypted.

The graphic code 703 is characteristic of a certain treatment chair, 704 is characteristic of a certain dialysis machine, 705 is characteristic of a certain accessory part 708, embodied here as a canister, for example, 706 is characteristic of a certain blood tubing 101 and 707 is characteristics of a certain dialysis filter 103. All the graphic codes can be generated individually and uniquely for each individual part. The same parts such as dialysis filters may also be provided with an individual identification feature to permit an unambiguous allocation.

In agreement with the teaching of the present invention, a mobile computer can also enter all parts characterized in this way at a treatment station and decode them. Next the mobile computer can forward the information thus obtained, namely which parts of a treatment station work together.

This forwarding may be performed by a data transmission to a remote computer, for example, to a server, where the information is stored. If the patient identifies himself on the dialysis unit, for example, by entering his patient card on the dialysis machine, then the dialysis machine can transmit the patient's identity to the remote computer, for example, by a remote data transmission. Together with the patient's identity, an identification feature of the dialysis machine may also be transmitted. In this way the allocation between the concrete dialysis machine and the patient's identity may be performed in the remote computer.

Due to the fact that the parts assigned to the dialysis machine within a treatment station and which are provided with a graphic code may optionally have also been identified to the dialysis machine in the remote computer, where they are paired with one another, it is therefore sufficient for a dialysis physician, for example, to enter any graphic code within the treatment station with a mobile computer to have the identity of the patient transferred from the remote computer. In addition, besides the patient's identity and abundance of other information, for example, information about the current course of treatment which has been transmitted from the dialysis machine to the remote computer, or the total equipment at the respective treatment station, as known to the remote computer, may also be transmitted in addition to the patient's identity. Furthermore, an overview of the overall situation within a dialysis unit having multiple treatment stations may also be transmitted if these data are available in the remote computer and are allocated to one another.

Figure 8:
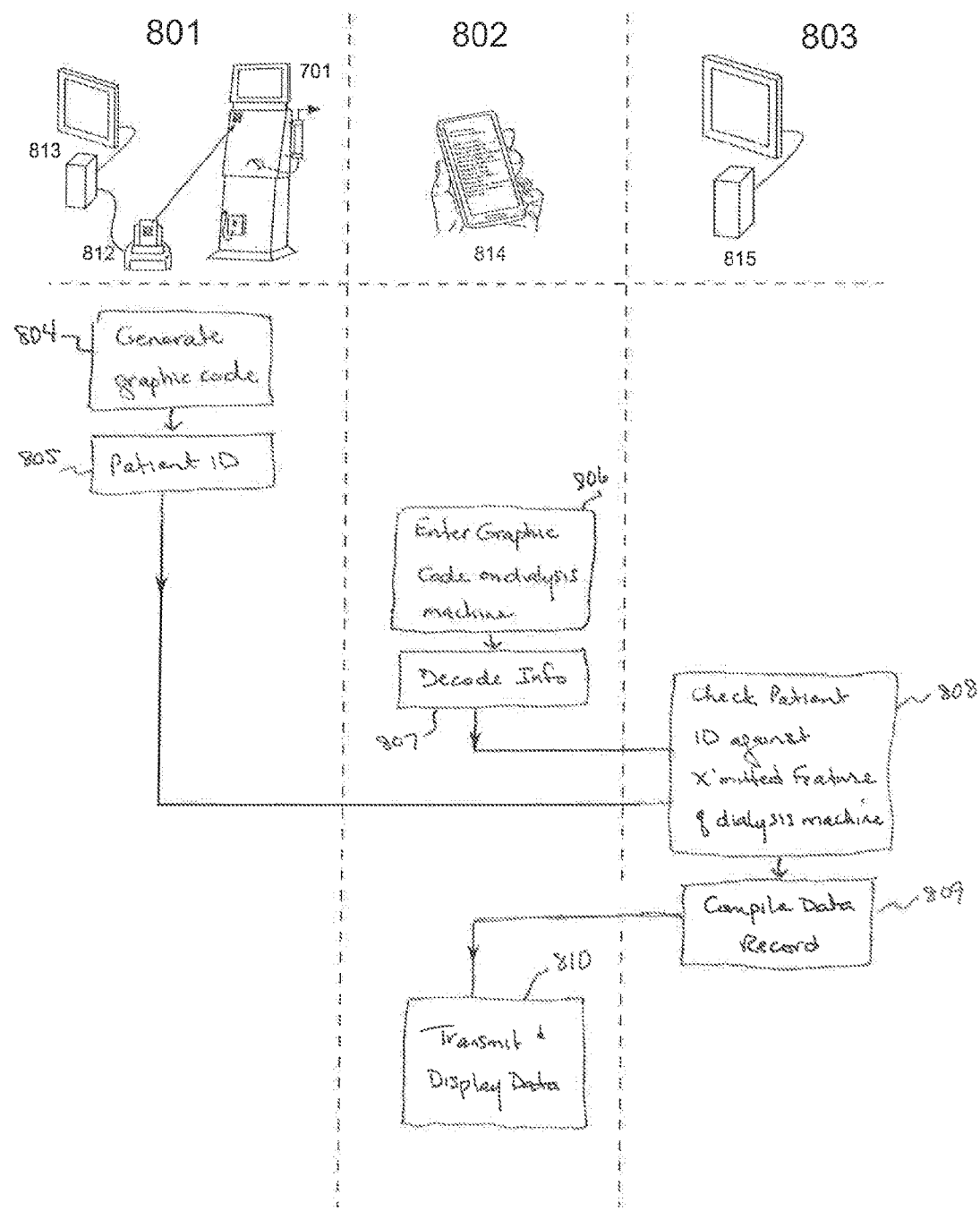
FIG. 8 shows a flow chart of a method for determining at least the patient's identity in accordance with the teaching of the present invention.

FIG. 8 shows as an example a flow chart for a system which permits the display of patient data on a mobile computer by entering a graphic code in accordance with the teaching of the present invention. FIG. 8 is subdivided into three columns 801, 802 and 803 to identify which steps are being performed by which machines. A system comprised of a computer 813 which may be equipped with a printer 812 and a dialysis machine 701 is involved in the steps performed in column 801. Column 802 identifies steps that are performed by a mobile computer 814, embodied there as a smartphone, for example. Column 802 identifies steps performed by a remote computer 815, which may be identical to the computer 812.

First in step 804, the graphic code specific for the respective dialysis machine is generated on the computer 813. To do so, at least one unambiguous identification feature such as individual machine numbers or fixed IP addresses at which dialysis machines communicate in a data network or MAC addresses (media access control addresses), which unambiguously identify the hardware of dialysis machines, is entered into a computer program being run on the computer 813. This computer program is programmed so that it encodes the identification feature in a graphic code, for example, a QR code.

Next, this graphic code is applied to the dialysis machine. This may be done by applying a stick-on label, which was previously created with the help of a printer 813 and which has the graphic code is applied to the dialysis machine.

In step 805, a patient identifies himself to the dialysis machine. This may be done, for example, when the patient enters his patient card into the dialysis machine. Next, the patient's identity together with the identification feature of the dialysis machine is transmitted to the remote computer 815.

In step 806, the graphic code is entered on the dialysis machine 701 using a reading device, for example, a camera on the mobile computer. Through appropriately programmed software running on the mobile computer, the coded information is decoded in step 807. Next information is transmitted, i.e., at least the identification feature of the dialysis machine 701 is transmitted to the remote computer 815, for example, by remote data transmission.

In step 808 appropriately programmed software running on the remote computer 815 checks on which patient's identity has been assigned to the transmitted identification feature of the dialysis machine 701. Then in step 809, a data record is compiled, including at least the patient's identity. In addition, further patient-related information may also be present in this data record, for example, treatment data, physiological data or the like.

Next this data is transmitted to the external computer and is processed there for the user and then displayed in step 810.

Figure 9:
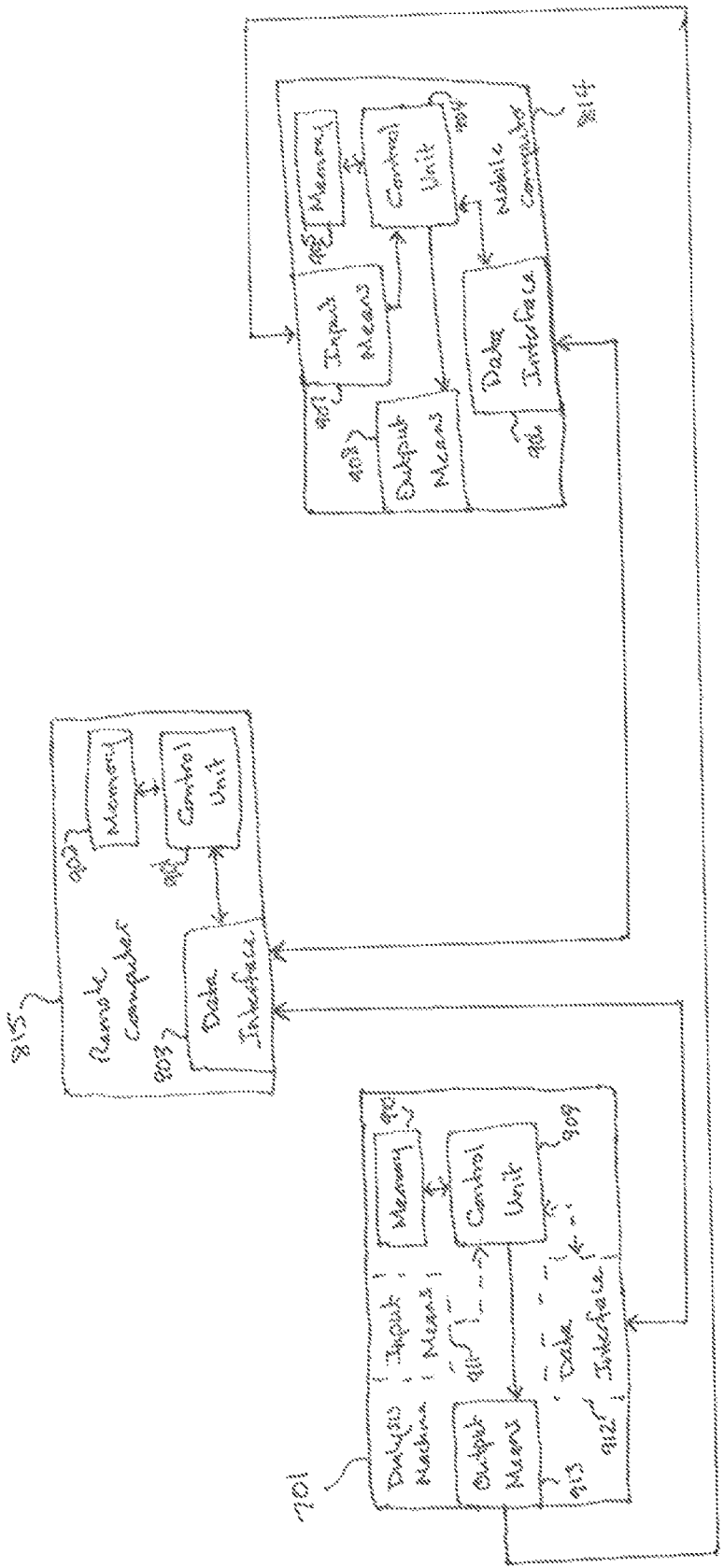
FIG. 9 shows a symbolic representation of a system comprised of a medical machine, a mobile computer and another computer for determining at least the patient's identity, in accordance with the teaching of the present invention.

FIG. 9 shows a diagram of the machines that can implement the embodiments of the methods described here and their components in accordance with the teaching of the present invention.

The dialysis machine 701 here, the remote computer 815 and the mobile computer 814 each include at least one control unit 909, 904 and 901, each of which can access a memory 910, 902 and 905.

Software programs that program the control unit, so that it can execute the methods described here in accordance with the teaching of the present invention, are stored in these memories.

The mobile computer 814 and the remote computer 815 therefore each have a data interface 906 and 903 by means of which they can exchange data with other devices. Such interfaces may be, for example, network interfaces or mobile radio devices.

In addition, the mobile computer has at least one input means 907 by means of which the information can be made accessible to the control unit 904. One such input means may be a camera.

The information directed to a user may be output via the at least one output means 908. One such output means may be a display screen.

A touchscreen display, for example, is an example of a combined input and output means.

The dialysis machine 701 optionally comprises a data interface 912 and input means 911, symbolized by the dotted line presentation. The at least one output means 913 may be a combined input and output means, for example, a touchscreen display.

The dialysis machine can communicate with the remote computer via the data interface 912 in order to transmit to it the identity of a patient, for example, that has been entered on the input device, which in this case is configured as a card reader, and to transmit an identification feature, for example, to the remote computer. This is symbolized by the arrow between the data interfaces 912 and 903.

In the same way the mobile computer 814 can send information to the remote computer 815. For example, an identification feature, which is transmitted by entering, decoding and optionally decrypting a graphic code that has been entered may be transmitted.

The remote computer 815 may likewise send data over the data interface 903 to the mobile computer, for example, a patients identity associated with the identification feature transmitted by the mobile computer 814.

The data transmission from the dialysis machine 701 to the mobile computer 814 preferably takes place only via the optical pathway, for example, from the output device 913 over the input device 907 in the manner already described in that a graphic code displayed on the output device is entered with the input device 907.

In accordance with the teaching of the present invention, the graphic code may also be fixedly applied to the dialysis machine, for example, by a stick-on label.

In a preferred embodiment, a direct data transmission from the mobile computer 814 to the dialysis machine 701 is not provided in accordance with the teaching of the present invention, so that it is impossible to influence the dialysis machine 701 via the mobile computer 814, and in particular not through malicious software.

Figure 10:
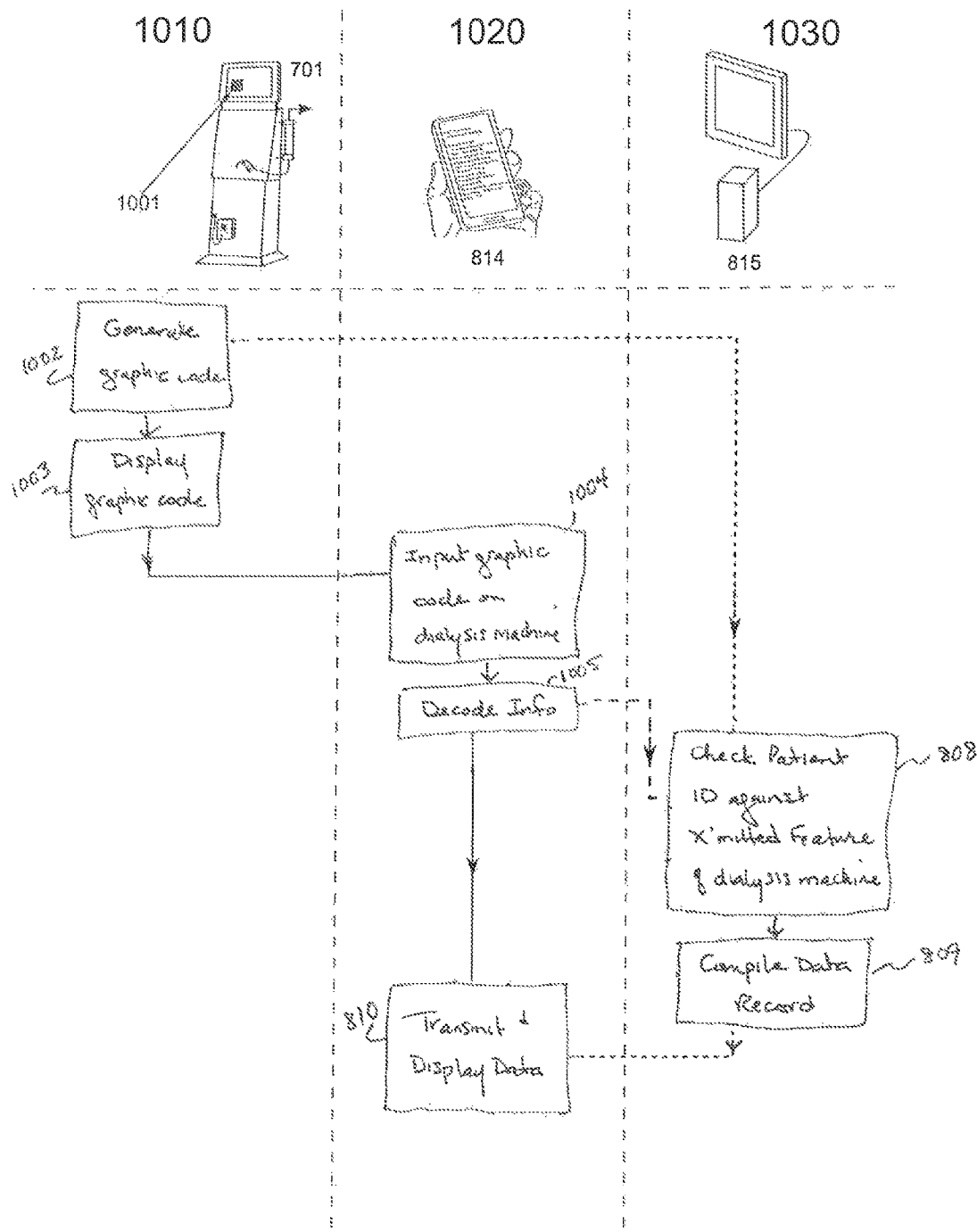
FIG. 10 shows the flow chart of a method for transmitting and displaying information which is specific for a medical fluid management machine or a treatment performed therewith on a mobile computer in accordance with the teaching of the present invention.

FIG. 10 shows as an example a flow chart for a method which permits the display of information on a mobile computer such that the information is specific for a medical fluid management machine and/or a treatment performed using said machine and encrypted specifically on the basis of the authorization of the group of people selected for receiving the information in accordance with the teaching of the present invention. FIG. 10 is divided into three columns 1010, 1020 and 1030 to identify which steps are performed by which machines. A dialysis machine 701 is involved in the steps which are performed in column 1010 as an example of a medical fluid management machine. Column 1020 identifies the steps performed by a mobile computer 814, embodied there as a smartphone, for example. Column 1030 identifies steps performed by a remote computer 815.

In step 1002, the graphic code 1001, which is specific for the medical fluid management machine and/or a treatment performed with it, is generated first. This graphic code may be encrypted at least in part in the manner already described, so that it can be decrypted only by those groups of people authorized to do so. This is achieved essentially in that a specific key which is available in decryption by a mobile computer used by the authorized person is used in the encryption.

In step 1003, this graphic code 1001 is displayed on a display device of the medical fluid management machine.

In step 1004, the graphic code is input on the dialysis machine 701 using a reader, for example, a camera on the mobile computer 814. Through suitably programmed software which is running on the mobile computer, the encoded and encrypted information is decoded in step 1005 and decrypted, if necessary. Depending on the authorization of the person doing the entering, the mobile computer therefore has one, more or no software key and can decode and decrypt the encrypted information accordingly and/or can decode official information. In a subsequent step 810, the decoded and optionally decrypted information is displayed.

The information contained in the graphic code 1001 may also contain the identity of the patient treated with the medical fluid management machine. Such information is preferably displayed in an encrypted form. A physician entering the graphic code 1001 on a mobile computer 814 can display this information by saving the proper key in the mobile computer.

The information contained in the graphic code 1001 may also include an identification feature of the medical fluid management machine. Like the method described in FIG. 8, the patient's identity may be transmitted by entering and decrypting the graphic code 1001 and sending the identification feature to a computer 815 via the mobile computer 814 and sending the patient's identity assigned to the identification feature in the computer 815 to the mobile computer 814. These method steps are optional and/or alternative and are also characterized by the broken lines in FIG. 10.

The invention claimed is:

1. A method for linking a plurality of dialysis treatment stations within a dialysis unit with a plurality of dialysis patients, respectively, each treatment station containing a dialysis machine and equipment cooperating therewith, said method comprising the steps of:

generating, for each of the dialysis treatment stations in the dialysis unit, a unique graphic code encoding an unambiguous identification feature of said each treatment station;

storing each graphic code, linked to the identification feature encoded thereby, in an allocation unit;

applying each graphic code to the treatment station identified thereby;

assigning the dialysis patients, individually, to individual treatment stations; transmitting the identity of each patient together with the encoded identification feature of the treatment station to which the patient is assigned to an allocation unit;

linking the identity of the patient to the encoded identification feature transmitted therewith, for each of the transmitted patient identities, at the allocation unit;

storing, in the allocation unit, a current course of dialysis treatment for each patient linked with one of said plurality of dialysis treatment stations within said dialysis unit; and providing a user of a mobile computer, by scanning therein any applied graphic code, with an overview including the identity of the patient assigned to each dialysis treatment station identified by the graphic code applied thereto, and the course of treatment for each assigned patient.

2. The method according to claim 1, wherein the applied graphic code is applied as a stick-on label to the treatment station.

3. The method according to claim 1, wherein the overview includes an occupancy of the dialysis unit including the identification of one or more patients currently being treated on one or more of said plurality of dialysis treatment stations, respectively, and a current treatment status of said one or more patients.

4. The method according to claim 3, wherein the current treatment status includes how long a dialysis treatment of each of said one or more patients will last.

5. The method according to claim 3, wherein the current treatment status includes which of said one or more patients are intended for a treatment within a certain interval of time in the future.

6. A method for determining and/or confirming the identity of a patient who has been treated or is to be treated at a treatment station of a dialysis unit having a plurality of dialysis treatment stations, each treatment station containing a dialysis machine and equipment cooperating therewith, said method comprising the steps of:
scanning a graphic code applied to the treatment station in the dialysis unit, which graphically encodes an unambiguous identification feature of the treatment station to which the graphic code is applied, into a mobile computer;
decoding the scanned graphic code to determine the encoded identification feature;
transmitting the decoded identification feature to an allocation unit storing a link between data relating to the patient being identified and the decoded identification feature, information pertaining to a current course of treatment for said patient, and information pertaining to course of treatment data for other patients linked, individually, with said plurality of dialysis treatment stations within said dialysis unit identified by the scanned graphic codes;
receiving at the mobile computer the patient's identity as determined and/or confirmed on the basis of the stored links of the patient to the identification feature and the identification feature to the applied graphic code; and
providing a user of the mobile computer, by scanned entry therein of one applied graphic code, with an overview that includes information on the plurality of treatment stations and information on each patient's course of treatment.

7. The method according to claim 6, wherein the patient's identity is displayed on the mobile computer.

8. The method according to claim 6, wherein additional patient-related information containing treatment data and/or physiological data is displayed on the mobile computer.

9. The method according to claim 6, wherein the applied graphic code is a barcode or a two-dimensional code.

10. The method according to claim 6, wherein at least one symbol is displayed within the applied graphic code.

11. The method according to claim 6, wherein the applied graphic code is a QR code.

12. The method according to claim 6, wherein the overview includes an occupancy of the dialysis unit including the identification of one or more patients currently being treated on one or more of said plurality of dialysis treatment stations, respectively, and a current treatment status of said one or more patients.

13. The method according to claim 12, wherein the current treatment status includes how long a dialysis treatment of each of said one more patients will last.

14. The method according to claim 12, wherein the current treatment status includes which of said one or more patients are intended for a future treatment within a certain interval of time.

15. A system for determining and/or confirming the identity of a patient that has been treated or is to be treated on a dialysis treatment station of a dialysis unit having a plurality of dialysis treatment stations, and for linking a plurality of dialysis patients with the plurality of dialysis treatment stations, said system comprising:
a dialysis unit having a plurality of dialysis treatment stations, each station containing a dialysis machine and equipment cooperating therewith, and each dialysis treatment station having a unique graphic code applied thereto which graphically encodes an unambiguous identification feature of the treatment station to which the code is applied;
an allocation unit storing a link between the identity of each patient and the unambiguous identification feature encoded by an applied graphic code and storing a link between each graphic code and the unambiguous identification feature of the treatment station encoded thereby, said allocation unit being configured to store information pertaining to each patient and a current course of treatment for each patient, said allocation unit also configured for storing information pertaining to the equipment cooperating with the dialysis machine of each treatment station having an applied graphic code; and
a mobile computer having a control unit, a display, a data interface and a reader for scanning each applied graphic code, said control unit being configured to decode the identification feature encoded in each applied graphic code, and the data interface being configured to transmit the identification feature decoded from each applied graphic code to said allocation unit and to receiving the identity of the patient assigned to the treatment station to which the scanned graphic code is applied from the allocation unit as a result of the transmission, said data interface being configured to provide a user of the mobile computer, by scanning therein the graphic code applied to any of the treatment stations using the reader, with an overview presented on the display that includes information on the plurality of treatment stations within the dialysis unit, information on each patient assigned a treatment station, information on each assigned patient's course of treatment, and information on said equipment cooperating with each treatment station having an applied graphic code.

* * * * *